United States Patent [19]

Spademan

[11] Patent Number: 5,002,045
[45] Date of Patent: * Mar. 26, 1991

[54] CUFF DEVICE

[76] Inventor: Richard G. Spademan, 2600 Capitol Ave., Ste. 405, Sacramento, Calif. 95816

[*] Notice: The portion of the term of this patent subsequent to Mar. 17, 2004 has been disclaimed.

[21] Appl. No.: 437,966

[22] Filed: Nov. 24, 1989

Related U.S. Application Data

[63] Continuation-in-part of Ser. No. 204,666, Jun. 10, 1988, abandoned, which is a continuation-in-part of Ser. No. 168,702, Mar. 16, 1988, Pat. No. 4,856,500.

[51] Int. Cl.⁵ .......................... A61F 5/04; A61F 2/78; A61F 5/01
[52] U.S. Cl. ................................ 128/80 C; 128/80 F; 128/88
[58] Field of Search ................. 128/80 C, 80 F, 80 G, 128/88

[56] References Cited

U.S. PATENT DOCUMENTS

| | | | |
|---|---|---|---|
| 73,768 | 1/1968 | Allen | 128/88 |
| 1,601,659 | 9/1926 | Van Harlingen | 128/80 C |
| 2,195,024 | 3/1940 | Bullock | 128/88 |
| 2,467,907 | 4/1949 | Peckham | 128/88 |
| 2,558,986 | 7/1951 | Seelert | 128/80 F |
| 4,088,130 | 5/1978 | Applegate | 3/22 |
| 4,220,148 | 9/1980 | Lehneis | 128/80 C |
| 4,320,747 | 3/1982 | Daniell, Jr. | 3/22 |
| 4,340,041 | 7/1982 | Frank | 128/80 C |
| 4,361,142 | 11/1982 | Lewis et al. | 128/80 C |
| 4,428,369 | 1/1984 | Peckham et al. | 128/80 C |
| 4,506,661 | 3/1985 | Foster | 128/88 |
| 4,649,906 | 3/1987 | Spademan | 128/80 C |
| 4,856,500 | 8/1989 | Spademan | 128/80 C |

FOREIGN PATENT DOCUMENTS 3320274 12/1984 Fed. Rep. of Germany .
2122846 9/1972 France .
1213855 11/1970 United Kingdom .

OTHER PUBLICATIONS

Supplementary European Search Report EP 88 90 5562 of 01/22/90.

Primary Examiner—Edgar S. Burr
Assistant Examiner—Moshe I. Cohen
Attorney, Agent, or Firm—Townsend and Townsend

[57] ABSTRACT

A dynamic support (1, 30) is disclosed in which there is provided a fitting system (2, 31) for engaging body parts articulated to each other, arms (4, 5) attached to and extending from the fitting system and movable in attachment to each other remote from the fitting system, and tightening cables (19, 45) attached to the fitting system for dynamically temporarily tightening and balancing the fitting system on the body parts in response to movement of one body part relative to the other body part.

13 Claims, 4 Drawing Sheets

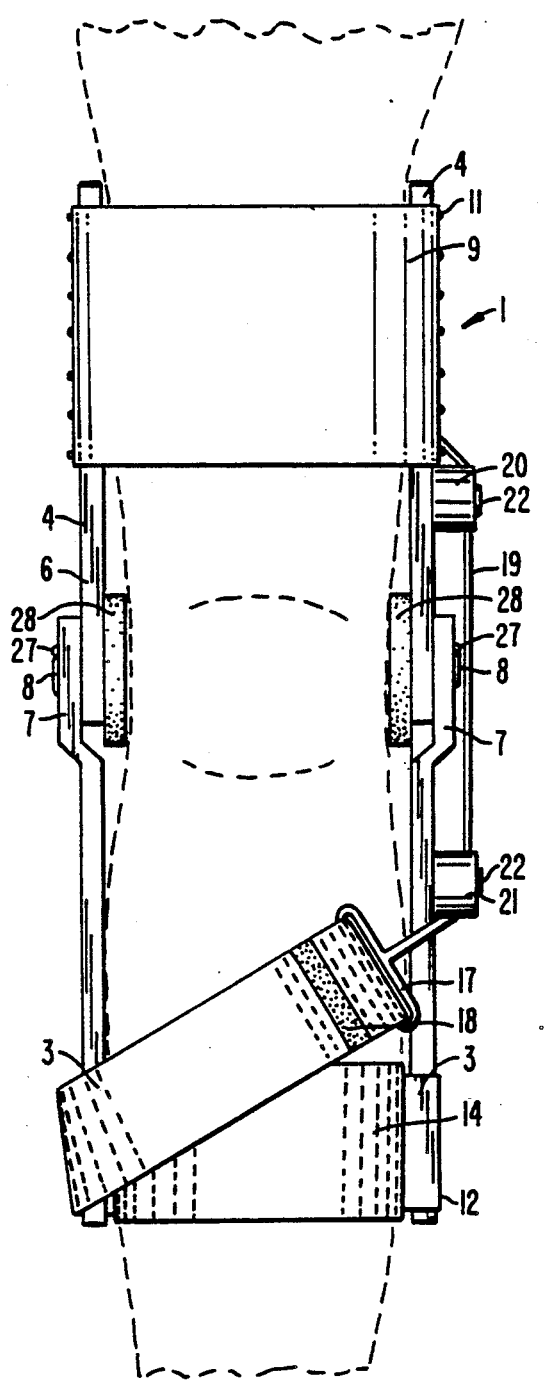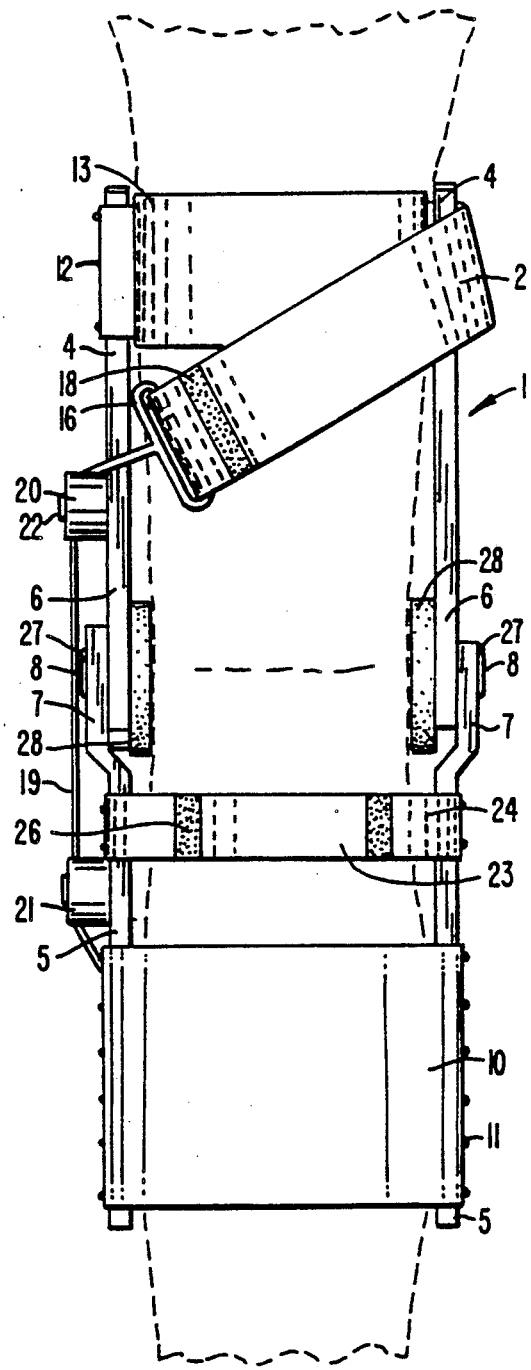
FIG._1.   FIG._2.

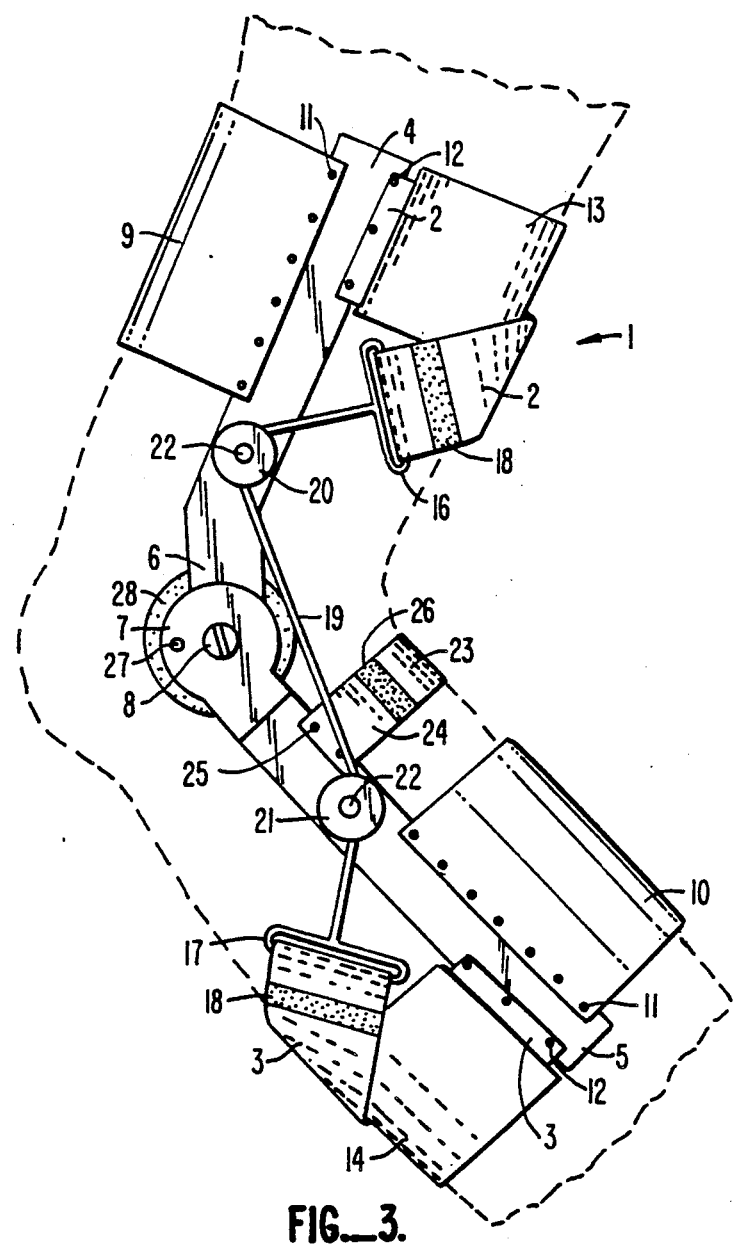
FIG._3.
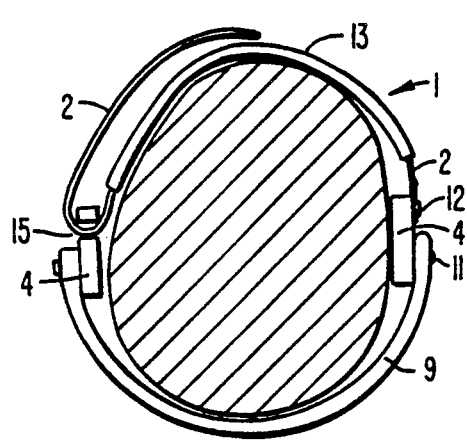
FIG._5.

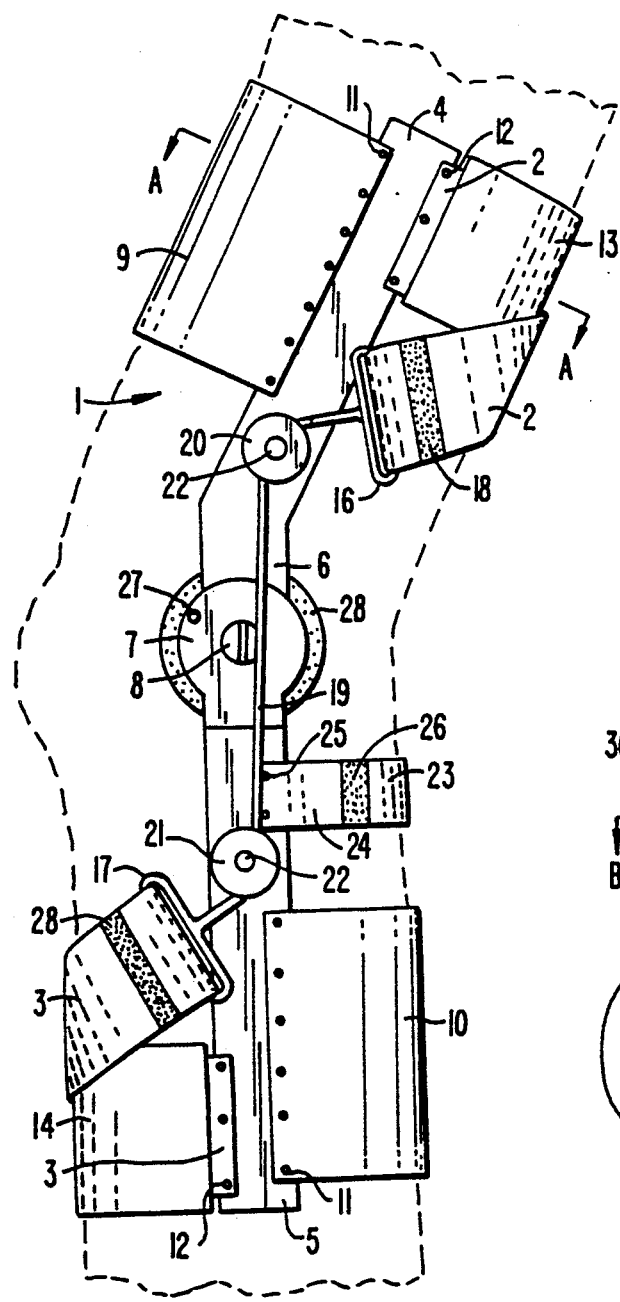
FIG._4.
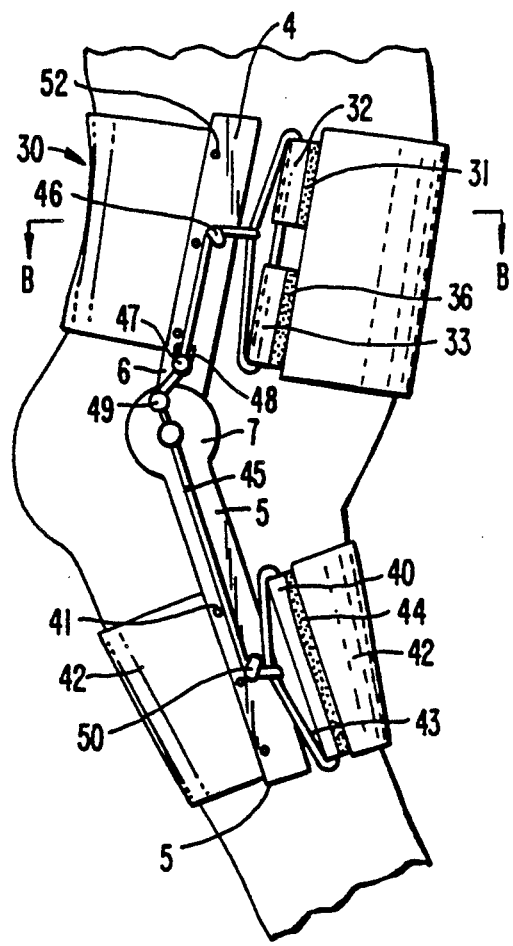
FIG._7.

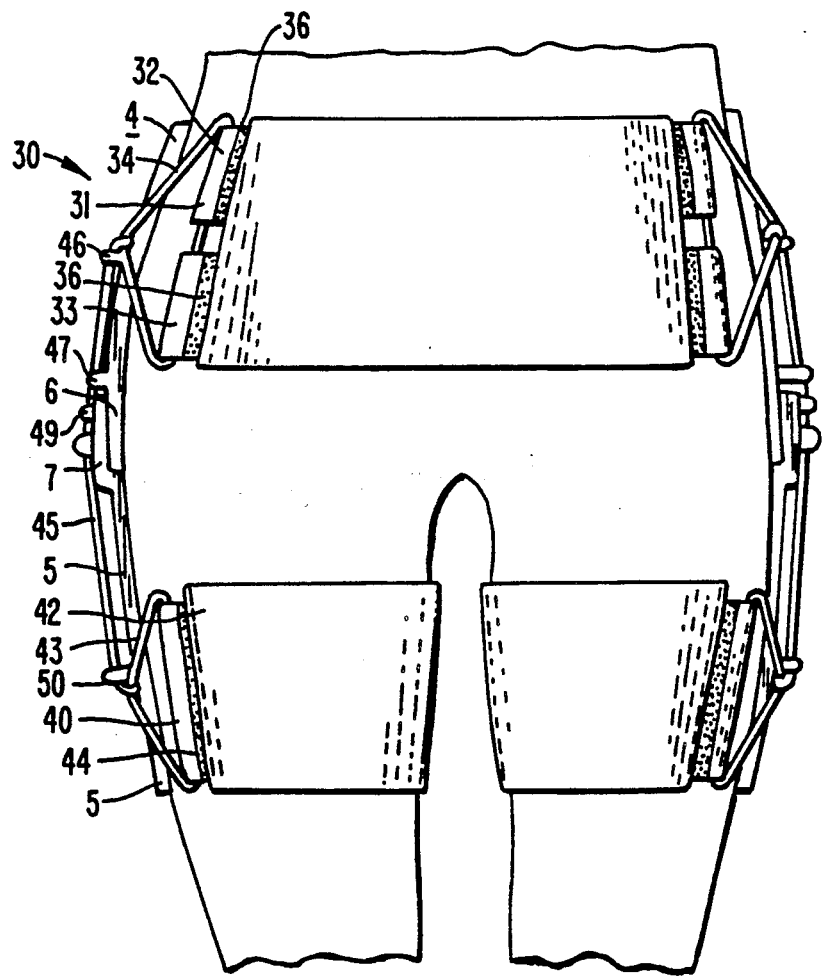
FIG._6.
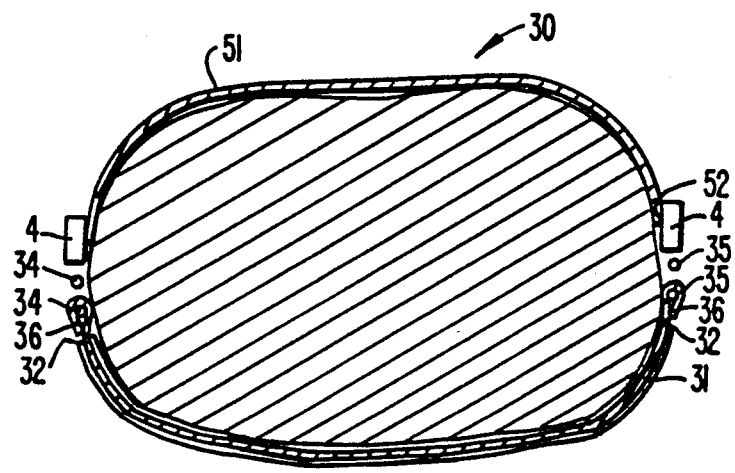
FIG._8.

CUFF DEVICE

BACKGROUND OF THE INVENTION

This is a continuation-in-part of U.S. patent application Ser. No. 07/204,666, filed June 10, 1988, now abandoned; which was a continuation-in-part of Ser. No. 168,702, filed Mar. 16, 1988, now U.S. Pat. No. 4,856,5000 issued Aug. 15, 1989.

The present invention relates to therapeutic and prophylactic devices, particularly to a cuff device or dynamic support that temporarily tightens and loosens on a wearer's body part as another body part is moved.

Various compressive cuff devices are known such as the straps that hold braces on a patient's limb and trunk to protect ligaments, tendons and bones as they heal following injury or surgery. Various strapping devices are also used to help prevent injury or provide support for the chronic instability of a body part. Elastic stockings and inflatable cuffs are used to reduce edema and blood stasis in the extremities that result from disease, injury, prolonged confinement or surgery.

Unfortunately, at the present time, ideal conditions for the efficient application of these braces, cuffs and stockings cannot be achieved with conventional means. These supporting structures tend to be either too loose on the body part, in which case the support members cannot adequately stabilize the body part against undesirable or abnormal movement or fluid stasis or, more frequently, these supporting structures are held too tightly, intensifying discomfort, prolonging immobility and aggravating the problem of stasis or atrophy.

SUMMARY OF THE INVENTION

It is accordingly a primary object of the present invention to provide a cuff device or dynamic support that overcomes the drawbacks of previously known devices of the above known type.

Another object of the present invention is to provide a dynamic support that momentarily tightens on a body part in response to movement of another body part.

It is still another object of the present invention to provide a dynamic support that temporarily tightens and loosens from a close fit or snug fit position on a body part in desirable directions but not in other directions.

It is still another object of the present invention to provide a dynamic support that can be adjusted to control the rate and amount of tightening and loosening of the dynamic support on a body part in response to a predetermined movement in a predetermined direction from a predetermined position of another body part.

It is still another object of the present invention to provide a dynamic support that can temporarily tighten and loosen in more than one direction from a close fit or snug position on a body part in response to a predetermined movement in a predetermined direction from a predetermined position of another body part.

It is still another object of the present invention to provide dynamic supports that can temporarily tighten and loosen from a close fit or snug position on the body parts and balance the tightness of the supports in response to a predetermined movement in a predetermined direction from a predetermined position of one of the body parts.

BRIEF DESCRIPTION OF THE DRAWINGS

In the drawings:

FIG. 1 is a front elevation view of the dynamic support in an extended position.

FIG. 2 is a back elevation view of the dynamic support in an extended position.

FIG. 3 is a side elevation view of the dynamic support in a flexed position.

FIG. 4 is a side elevation view of the dynamic support in an extended position.

FIG. 5 is a vertical sectional view taken along line A—A of FIG. 4.

FIG. 6 is a front elevation view of the dynamic support of an alternative embodiment of the present invention.

FIG. 7 is a side elevation view of the dynamic support of the alternative embodiment of the present invention showing the pivot and cable assembly pivoted from the resting position.

FIG. 8 is a vertical sectional view taken along line B—B of FIG. 7.

DESCRIPTION OF THE PREFERRED EMBODIMENTS

Referring to FIGS. 1-5, a cuff device or dynamic support for the lower extremity and particularly the knee, is shown, but it is understood that the principles of the invention are also applicable to other articulated body parts. There is shown in FIG. 1 a dynamic support 1 which includes an upper or first body part engaging cuff component 2 and a lower or second body part engaging cuff component 3. These cuff components comprise a fitting system and are respectively adapted to engage the body parts above and below the body articulation.

A pair of arms 4 and 5 are respectively attached to and extend toward each other from the body part engaging cuff components 2 and 3. A set of these arms are located on opposite sides of the extremity. Each of these arms 4 and 5 terminate in movable overlapping end regions 6 and 7 remote from the cuff components and are formed with aligned openings through which a single pivot pin 8 extends. A more complex slidable and pivotable orthotic joint can be used. The orthotic joint can incorporate a rivet limit stop 27 known per se. The pivotable orthotic joint may also incorporate a condylar pad 28 known per se secured to the pivot pin 8. End region 7 pivots freely about pivot pin 8. Thus, pivot pin 8 forms a pivot axis which is generally perpendicular to the arms 4 and 5 and which coincides with the predominant axis to which swinging of the upper and lower body parts are limited. The arms 4 and 5 can be of a slightly flexible material construction such as metal or plastic. There is an anterior thigh upper cross member 9 and posterior calf lower cross member 10 which can be made of a slightly flexible formable material such as metal or plastic as are the arms 4 and 5 and can be shaped to conform to the body part such as the thigh and leg with heat and shaping tools. The opposite ends of each of the cross members 9 and 10 are fixed to the ends of each set of the arms 4 and 5 respectively by rivets 11 or the like.

The upper cuff component 2 and the lower cuff component 3 are constructed of slightly yieldable material such as plastic or cloth to conform to the body part configuration. Each of the cuff components 2 and 3 are attached at one end to one of the arms 4 and 5 respectively by rivets 12 or the like. The cuff components 2 and 3 pass through sleeves 13 and 14
e material respectively which are constructed of neopren or the like, pass through a slot 15 located toward the end of one of the uprights 4 and 5, as shown in FIG. 3, pass through loops 16 and 17 respectively and are adjustable and releasable in fixation to themselves by VELCRO brand hook and loop strip 18 or the like. The loops 16 and 17 are attached to a cable 19 which passes through guide 20 and guide 21 attached to one set of the arms 4 and 5 respectively by a bolt 22 or the like. Straps 23 and 24 are each attached at one end to one of the opposite arms 5 by rivets 25 or the like and are adjustable and releasable in fixation to each other by a VELCRO brand hook and loop strip 26 or the like. Straps 23 and 24 resist forward migration on the knee of end regions 6 and 7.

Movement of hinging end regions 6 and 7 cause the cable 19 to tighten cuff components 2 and 3 on the extremity by relative shortening of the cable 19 when the thigh is moved to an extended position relative to the leg from the flexed position. The segment of the upper cuff component 2 and lower cuff component 3 that pass through the sleeves 13 and 14 respectively tighten generally transverse the long axis of the body part. The segment of the upper cuff component 2 and the segment of the lower cuff component 3 that do not pass through the sleeves 13 or 14 respectively also tighten with a torsional component in generally opposite directions on the first and second body parts. Since the upper and lower cuff components are connected by the cable 19 there will be a balancing of the amount of tightening of the upper and lower cuff components.

Referring to FIGS. 6-8, there is provided in accordance with another embodiment of the present invention, a dynamic support designated generally as 30. Except as hereinafter described, dynamic support 30 is substantially identical to the dynamic support 1 and operates in the same manner with a tightening system for dynamically and momentarily tightening the cuff components on the body parts from the snug close fit position. Those features of the dynamic support which are identical to those of the dynamic support of FIGS. 1-5 are identified using the same numbers used in FIGS. 1-5. Comparable components can be located on each, side of the body. Arms 4 and 5 and end regions 6 and 7 and pivot pin 8 operate in the same manner as those parts shown in FIGS. 1-5.

An upper or first body part engaging cuff component 31 can be constructed of slightly yieldable material such as plastic or cloth and consists of a plurality of straps 32 and 33 which pass, on each end, through a loop 34 on each side of the first body part or trunk. Each strap 32 and 33 is adjustable and release in fixation to itself by a VELCRO brand hook and loop strip 36 or the like. A lower or second body part engaging cuff component 40 constructed of slightly yieldable material such as plastic or cloth is attached at one end to lower arm 5 by rivets 41 or the like. The lower cuff component 40 passes through a sleeve 42, around the second body part or lower thigh and through a loop 43 and is adjustable and re-leasable in fixation to itself by a VELCRO brand hook and loop strip 44 or the like. The loops 34 and 43 are attached to a cable 45, which passes through guide 46 and guide 47 which is attached by a bolt in a slot 48 in upper arm 4, guide 49 on end region 7 and guide 50 on lower arm 5. The rate and amount of tightness of the upper and lower cuff components or dynamic supports can be adjusted by the position of guide 47 in slot 48.

There is a posteriorly located cross member 51 which can be made of slightly flexible formable material such as metal or plastic and can be shaped to conform to the body part, such as the trunk, with heat and shaping tools. The opposite ends of the cross member 51 are attached to the ends of each arm 4 by rivets 52 or the like.

In use, movement of hinging end regions 6 and 7 cause the cable 44 to tighten cuff components 31 and 32 on the trunk and thigh when the trunk and thigh are moved in flexion or extension from the resting position by the relative shortening of cable 45 as end region 7 pivots relative to end region 6 increasing the distance between guide 47 and guide 48.

Details have been disclosed to illustrate the invention in a preferred embodiment of which adaptation and modification within the spirit and scope of the. invention will occur to those skilled in the art. For instance, the pivot and cable assembly can be incorporated into a dynamic support or cuff device to tighten and loosen from the close fit resting position on various body parts such as the trunk and shoulder, arm and forearm and wrist and hand. The scope of the invention is limited only by the following claims.

What is claimed is:

1. A dynamic support for first and second body parts which are articulated to each other comprising cuff components adapted to engage the first and second body parts when the first and second body parts are in a resting position, the cuff components engaging the first and second body parts at locations spaced from the body area where the body parts are articulated, arms attached to and extending from each of the cuff components and terminating in end regions, said end regions being movable in attachment to each other at a point adjacent to the area where the body parts are articulated, a tightening system attached to the cuff components, said dynamic support being characterized in that the tightening system includes members responsive to a predetermined relative movement between the body parts in more than one direction away from the resting position for increasing the tightness with which the cuff components engage the body parts.

2. A dynamic support according to claim 1 wherein said tightening system includes members responsive to a predetermined relative movement between the body parts in extension for increasing the tightness with which the cuff components engage the first and second body parts.

3. A dynamic support according to claim 1 wherein said tightening system includes members responsive to a predetermined relative movement between the body parts in flexion for increasing the tightness with which the cuff components engage the first and second body parts.

4. A dynamic support according to claim wherein said tightening system includes members for adjusting the rate and amount of tightness with which the cuff components engage the first and second body parts.

5. A dynamic support according to claim wherein said tightening system includes members responsive to a predetermined relative movement between the body parts for balancing the tightness with which the cuff components engage the first and second body parts.

6. A dynamic support according to claim 5 wherein said tightening system includes at least one moveable member connecting the cuff components.

7. A dynamic support according to claim 6 wherein said connecting member comprises a cable.

8. A dynamic support according to claim 1 wherein said cuff components tighten generally with a torsional component.

9. A dynamic support according to claim 8 wherein said torsional component tightens in generally opposite directions on said first and second body parts.

10. A dynamic support according to claim 1 wherein said arms are located on each side of the body part.

11. A dynamic support according to claim 1 wherein said tightening system is attached to at least one arm.

12. A dynamic support according to claim 10 wherein said arms are connected by at least one formable cross member.

13. A dynamic support for first and second body parts which are articulated to each other comprising cuff components adapted to engage the first and second body parts when the first and second body parts are in a resting position, the cuff components engaging the first and second body parts at locations spaced from the body area where the body parts are articulated, arms attached to and extending from each of the cuff components and terminating in end regions, said end regions being movable in attachment to each other at a point adjacent to the area where the body parts are articulated, a tightening system attached to the cuff components, said dynamic support being characterized in that the tightening system includes members responsive to a predetermined relative movement between the body parts in more than one direction for balancing the tightness with which the cuff components engage the body parts.

* * * * *